(12) United States Patent
Carnevali

(10) Patent No.: US 6,391,323 B1
(45) Date of Patent: May 21, 2002

(54) COMPOSITION FOR THE TREATMENT OF BURNS, SUNBURNS, ABRASIONS, ULCERS AND CUTANEOUS IRRITATION

(76) Inventor: Andrea Carnevali, Via Pedica 120-00046, Grottaferrata (IT)

( * ) Notice: Subject to any disclaimer, the term of this patent is extended or adjusted under 35 U.S.C. 154(b) by 0 days.

(21) Appl. No.: 09/555,008

(22) PCT Filed: Nov. 24, 1998

(86) PCT No.: PCT/IT98/00339

§ 371 Date: May 23, 2000

§ 102(e) Date: May 23, 2000

(87) PCT Pub. No.: WO99/26589

PCT Pub. Date: Jun. 3, 1999

(30) Foreign Application Priority Data

Nov. 26, 1997 (IT) ........................................ RM97A0731

(51) Int. Cl.[7] ............................ A61K 7/00; A01N 65/00; A01N 25/00; A01N 55/02; A61L 15/00
(52) U.S. Cl. ........................ 424/401; 424/445; 424/443; 424/78.06; 424/400; 424/725; 514/185; 514/887; 514/947; 514/974; 514/828
(58) Field of Search ................................ 424/401, 445, 424/443, 78.06, 400, 725; 514/185, 887, 947, 974, 828

(56) References Cited

U.S. PATENT DOCUMENTS

| 2,120,667 A | | 6/1938 | Gruskin | |
|---|---|---|---|---|
| 2,729,586 A | | 1/1956 | Peck | |
| 3,949,071 A | | 4/1976 | Alnor | |
| 4,778,673 A | * | 10/1988 | Vernizzi et al. | ................ 424/10 |
| 4,797,392 A | * | 1/1989 | Chernomorsky | ............ 514/185 |
| 4,849,214 A | | 7/1989 | Ruiseco | |

OTHER PUBLICATIONS

Patent Abstracts of Japan, vol. 009, No. 104 for JP–59 231019 dated May 8, 1985.

* cited by examiner

*Primary Examiner*—Diana Dudash
*Assistant Examiner*—Clinton Ostrup
(74) *Attorney, Agent, or Firm*—Smith, Gambrell & Russell, LLP

(57) ABSTRACT

A composition having analgesic, antiseptic and skin healing promoting activity, suitable for the treatment of burns, sunburns, scalds, irritation, sores and abrasions which includes, as active ingredients, chlorophyll, cod liver oil, and camphor, preferably together with a natural antiseptic agent chosen from niaouli oil, thyme oil, and mixtures thereof, in a pharmaceutically acceptable vehicle for topical application.

11 Claims, No Drawings ns. The corresponding derivatives, known as
COMPOSITION FOR THE TREATMENT OF BURNS, SUNBURNS, ABRASIONS, ULCERS AND CUTANEOUS IRRITATION This application is a 371 of PCT/IT98/00339 filed Nov. 24, 1998.

The present invention concerns a composition for the treatment of burns, sunburns, abrasions, ulcers and cutaneous irritation. More specifically, the invention relates to a preparation for topical administration having analgesic, antiseptic and skin healing promoting activity. The preparation is particularly suitable for the treatment of burns, scalds and sunburns, and is useful in general in the treatment of any alteration of the dermal tissue that may require the reactivation of the epithelisation processes.

As it is known, the exposure to an excessive heat of any kind causes on the human epidermis, and often also on the underlying tissues, situations of pathological alteration and lesions the seriousness of which varies according to the duration and the intensity of the exposure, and to the sensitivity of the single individual. Real burns or scalds may be caused, for instance, by the contact with hot matter or articles, such as flames, hot liquids or burning bodies, or also by an excessive exposure to radiation sources, including the sun. According to the current clinical classification, a burn may be of first, second or third degree, depending upon the gravity of the lesion. The first-degree burns are limited to the superficial layers of the epidermis and are characterised by local erythema (redness) and light edema (swelling); the second-degree burns involve a damage extended to the dermis, more marked edema and formation of blisters containing serous exudate, and the third-degree burns are accompanied by a true destruction of the structural elements of the skin, with formation of blisters, sores and the presence, in the most serious cases, of charred zones. In the most critical cases the involvement is extended to general phenomena, such as shock, acute intoxication and anaemia.

Reactions quite similar to the ones described above may be produced by the contact with aggressive chemical agents, such as concentrated acids or alkalis, or by electrical discharges. Likely, albeit less serious, reactions may also originate from the contact of the skin with animal secretions or stinging plants, such as jellyfish stings or insect bites. Irritation, redness, itching and, sometimes, blister formation may also be caused by an intense rubbing of the skin, while a stronger rubbing may give rise to abrasions and grazes. Lastly, another quite common group of pathologies affecting the superficial tissues are ulcerous-dystrophic alterations, such as torpid sores, decubitus or bed-sore, varicose or stasis ulcers and rhagades.

In all of the cases presented above, in agreement with the various levels of severity, recourse is made to the topical administration of remedies that should exert a range of different actions, including an analgesic action, a stimulating action on the reparative processes of the skin tissues, i.e. an action promoting healing of the lesions, an antiinflammatory action and, moreover, an antiseptic action, in order to prevent the occurrence of secondary infections on the affected zones. Actually, the injured tissues are particularly prone to the development of infections, which obviously hinder a rapid and complete healing of the skin.

A product for topical application known to be particularly useful for the treatment of burns, scalds and sunburns, as well as for the treatment of other affections of the superficial tissues such as the disorders and injuries mentioned above, is the ointment sold in Italy under the trademark Foille® (Synthelabo). The latter contains four different active ingredients, i.e., benzocaine, benzyl alcohol, 8-hydroxy-quinoline and colloidal sulphur. The first two ingredients have anaesthetic properties, the third one is an antiseptic and the fourth one enhances the formation of stratum corneum (horny layer).

In the use of the above and of other possible remedies against burns, a timely application is extremely important. It may be anticipated that the therapy will be the more effective the shorter is the time elapsed between the event that caused the lesions and the application of the remedy on the said lesions. Suitable products may be in the form of ointments or salves, creams, emulsions, gels, foams, sprays or medicated dressings or bandages, which must be directly applied on the affected zone and must be kept into contact with the lesion, if necessary by soaking the dressing from the exterior with further product, until the reparative process is seen to stably proceed.

In such situations it would be desirable that the recovery time be as short as possible, not only because this reduces the pain or discomfort caused to the patient, but also because the longer the lesion remains exposed to the environment the higher is the risk of secondary infections. As pointed out in the foregoing, the latter obviously slow down or negatively affect the recovery process. In view of that, it is extremely important that a preparation for the treatment of skin lesions such as burns and the like be highly active in promoting the regeneration of the injured tissues, thus enhancing the healing process.

A product which is known to possess the above properties, and which may be used to formulate a medicament suitable for the treatment of burns and of other lesions of the skin is chlorophyll (see Merck Index, $11^{th}$ ed., 1989, Merck & Co. Inc., monograph No. 2155).

As it is known, chlorophyll is the green pigment of plants, contained in various proportions and types also in algae. The said pigment plays a primary role in the vegetal metabolic activity known as photosynthesis. The chlorophyll molecule, in its variants a, b, c and d, is characterised by an active nucleus known as porphyrin (a cyclic tetrapyrrolic structure wherein the four pyrrole rings are joined through four methene bridges, i.e.=C–) at the centre of which is bound a magnesium atom. Commercial chlorophyll is normally an intensely dark-green aqueous, alcoholic or oil solution, substantially containing chlorophyll a and chlorophyll b, i.e. the two variants that are found (in the approximate ratio of 3:1) in higher plants and in green algae. The most common uses of chlorophyll are in the production of soaps, oils, cosmetics and perfumes, as well as in the food industry, for the production of liquors and confectionery.

"The porphyrin structure of chlorophyll is the same found in heme, i.e. the prosthetic group of hemoglobin, wherein at the center of the molecule an atom of iron is present instead of the magnesium atom. It is, very likely, this similitude to the complex responsible for the cellular respiration that accounts for the interesting physiological properties of chlorophyll and, in particular, for its activity as promoter of the cutaneous restoration processes. It is to be noted, in addition, that one of the two carboxy groups pending from the porphyrin structure is esterified, in chlorophyll, with an unsaturated alcohol known as phytol. The latter is a constituent of vitamin E, the therapeutic properties of which are well-known."

An alkaline hydrolysis of chlorophyll in mild conditions causes the opening of the cyclopentanone ring present in the molecule and the replacement of both ester groups present (one of which is esterified with phytol) with alkaline metal ions. The corresponding derivatives, known as chlorophyllins, have been proposed as well for the treatment of ulcerative lesions and burns, especially in the presence of concomitant infection. Examples of such indication are found in the U.S. Pat. Nos. 2,120,667 and 2,729,7586.

With reference to the use of chlorophyll in preparations for the treatment of burns and sunburns, the U.S. Pat. No. 3,949,071 proposes the application to the injured skin area of a buffer solution having a pH value of 8–10 containing a base, preferably consisting of an alkaline metal carbonate; one or more surface-active agents; a mixture of unsaturated fatty acids; a volatile agent such as diethyl ether, the evaporation of which is supposed to cause some relief to the burnt skin and, as the proper active ingredients, eugenol, i.e. an essential oil known for its antiseptic properties, and chlorophyll. The latter, according to the disclosure, is believed to cause pigment production and thus contribute to the formation of a secondary protectant in the skin.

In view of the foregoing, the object of the present invention is to provide a preparation particularly suitable for the therapy of burns and sunburns, and also effective on the other types of cutaneous lesions and affections referred to above, which preparation is markedly active in promoting the reparative processes of the skin tissues—thanks to the presence of chlorophyll—and is, in addition, capable of performing all of the other actions that are requested to a medicinal product for the therapy of burns. Among these actions, the pain relieving and refreshing action and the antimicrobial action are of a major importance.

To achieve such purpose, the present invention proposes to add to chlorophyll some other natural active ingredients the combination of which results in a product of greatly enhanced activity and rapidity of action. The first one of the said additional ingredients is cod liver oil, the activity of which as healing promoter is known (see Merck Index, loc. cit., monograph No. 2464). Cod liver oil is obtained by extraction under pressure from the livers of fishes of the Gadidae species, and is substantially composed of fatty acids glycerides, specifically glycerides of palmitic, stearic, myristic and ricinoleic acid, of cholesterol and of remarkable amounts of vitamins A and D. The commercial product varies in colour from pale-yellow to brown, and has characteristic odour and taste, which become stronger and disagreeable on prolonged exposure to light and air.

Cod liver oil is traditionally used in medicine as a source of vitamins A and D, and is also employed, mainly in veterinary medicine, as a promoter of tissue healing. Such activity, however, does not appear to have been exploited in topical preparations for the treatment of burns and scalds.

According to the invention, the preparation also contains, as a primary ingredient, camphor or 2-bornanone (see Merck Index, loc. cit., monograph No. 1738) a cyclic ketone that is traditionally extracted from the wood (and also from the leaves and the roots) of the camphor tree (*Cinnamomum camphora*), by steam distillation. Once cooled, the essence crystallises to give a white mass, that is separated from the remaining aqueous liquid by filtration; by treating the said mass under mild pressure and temperature conditions an oil is separated, and the raw camphor is obtained as the residual solid, in the form of brown pieces. The latter is transformed into the commercial camphor by sublimation. Natural camphor consists of the D(+) isomer, that is the biologically active isomer. However, for industrial uses the racemic form, produced synthetically (e.g., from pinene), is also widespread.

Camphor is currently employed for several applications, such as the production of moth repellents and deodorant mixtures, and the manufacture of plastics (especially celluloid), lacquers and varnishes, where it is added as a plasticiser. In the field of phytotherapy camphor is used as a liniment for the treatment of muscular and arthritic pain, as a mucolytic and antispasmodic agent for the upper respiratory tract infections and as a tonic for the circulatory system. The acknowledged pharmacological activities of camphor are on one hand the activity as a topical anaesthetic and analgesic (e.g., against itching and irritation) and, on the other hand, the antiseptic and anti-infective activity. Both the foregoing properties are found to be extremely advantageous for the purposes of the present invention.

Accordingly, the present invention specifically provides a composition for the treatment of burns, sunburns, abrasions, ulcers and cutaneous irritation comprising, as active ingredients, chlorophyll, cod liver oil and camphor in a pharmaceutically acceptable vehicle for topical application. The preferred amounts of the said three main ingredients are from 0.5 to 5 percent by weight of chlorophyll, from 5 to 10 percent by weight of cod liver oil and from 5 to 10 percent by weight of camphor.

Preferably, the proposed composition comprises further ingredients with antiseptic activity, specifically one or both the natural essences known as niaouli oil and thyme oil. Niaouli oil is an essential oil obtained by steam distillation from the fresh leaves of *Melaleuca viridiflora*, the main components of which are 1,8-cineole, $\alpha$-terpineol, $\alpha$-pinene and limonene. Such essence is also known commercially as gomenol, and is used in the disorders of the upper respiratory tract, as a balsamic and expectorant agent and, above all, as an anti-infective agent.

Thymus is in turn an active ingredient obtained from the dried leaves and flowers of *Thymus vulgaris* (common thyme) and of *Thymus zygis* (Spanish thyme), each taken separately or mixed together. The essential oil and the dried herb contain as the active ingredient thymol, which is known to be active as an antiseptic of the respiratory tract, for use both in topic preparations (administration by inhalation or instillation) and in preparations for systemic use (oral administration).

According to some specific embodiments, the composition of the invention comprises the three main ingredients in the proportions specified above and, in addition, from 5 to 10 percent by weight of niaouli oil and from 2 to 5 percent by weight of thyme oil.

A preferred formulation of the composition according to the invention is as follows (all of the percentages being by weight):

| | |
|---|---|
| chlorophyll | 1% |
| cod liver oil | 8% |
| camphor | 8% |
| niaouli oil | 8% |
| thyme oil | 3.5% |
| excipients | q.s. to 100% |

The non-active carriers or excipients may be chosen among the products conventionally employed in the pharmaceutical art for the formulation of products for topical application. In particular, one or more of the following ingredients may be used: anhydrous lanolin, paraffin, white wax, sweet almond oil, boric acid and/or salts thereof, mono-, di- and triglycerides of fatty acids, non-ionic surfactants and polyethylene glycol. Among the excipients there may be advantageously added, in particular, calendula oil. This product is known to be active in softening and protecting the skin. According to some specific embodiments of the invention the excipient exclusively consists of anhydrous lanolin, while according to other embodiments the said excipient is a mixture of boric acid, paraffin, white wax and sweet almond oil.

The composition according to the invention may be produced in the pharmaceutical forms commonly employed for the therapy of burns and cutaneous lesions, such as ointments, salves, creams, emulsions or gels. The different forms are obtained by appropriately choosing the nature and the proportions of the excipients. The composition of the invention may also be marketed in the form of medicated dressings or bandages.

In use, the product should be spread in a uniform layer on the injured area, and the application should be repeated two or three times a day by adding a thin layer of ointment from the exterior of the dressing, without removing the latter, if possible, for 24 hours.

A specific embodiment of the invention is described for merely illustrative purposes, together with the results of the experimentation carried out on the composition of the invention.

EXAMPLE

A preparation in the form of an ointment was produced from the following ingredients:

| | |
|---|---|
| chlorophyll | 3 g |
| cod liver oil | 24 g |
| camphor | 24 g |
| niaouli oil | 24 g |
| thyme oil | 10.5 g |
| anhydrous lanolin | q.s. to 300 g |

The production was carried out by softening lanolin so as to make it pourable, by heating it in a water bath to 30–40° C., then adding in sequence, while stirring, all of the other ingredients of the composition except chlorophyll. Stirring was continued until complete homogenisation of the mixture, and after the mixture had cooled down, chlorophyll was added, still with continuous stirring. The addition of chlorophyll is made at a lower temperature in order to avoid any risk of heat degradation of the product.

The above preparation was employed in a series of clinical trials, in particular on sunburns and burns of varying extent and seriousness, in order to evaluate the efficacy of the proposed remedy. In most cases clear improvements of the patient conditions were evident after one of two days from the first application, thus showing the remarkable activity and rapidity of action of the preparation according to the invention. Some of the observed cases are reported below.

$1^{st}$ case—Sunburn—A young man had been exposed to actinic radiation, bare-chested, for several hours in a hot summer day. As a result, his skin had turned deep-red and aching, and he could not stand the contact of clothes over the burnt zone. The ointment according to the invention was thus applied in a thin and uniform layer over the affected area. The day after the erythema had totally disappeared, and, moreover, the epidermis had not suffered from any damage. The suntan was maintained over the following days.

$2^{nd}$ case—Second-degree burn—A young woman had a calf burned by the contact with the hot exhaust head of a motorbike. The ointment of the invention was spread on the injured area after about 20 minutes from the occurrence of the burning accident. As a result of the therapy, no blister formed on the injured area and the reddening regressed and completely disappeared within 24 hours. Some time after the recovery, no scars or traces were visible that could evidence any permanent damage suffered by the skin.

$3^{rd}$ case—Sunburn—A young man had his face burned by an exaggerate exposure to the sun in the high mountains. The skin on his face was deep-red, except the ocular zone, which had been protected by the sunglasses. The ointment of the invention was thus applied on the patient's face, carefully avoiding the eyes and the mucous membranes, where the camphor present in the composition might cause some discomfort. The day after, both pain and erythema had totally disappeared, and the formerly affected area had taken a suntan colour.

$4^{th}$ case—Scald from boiling oil—An elderly woman had one arm and one leg burned by boiling oil poured from a hot pan. The ointment according to the invention was uniformly applied on, the whole injured area after less than one hour from the accident. The patient felt an immediate relief from pain. The affected epidermal areas were kept soaked with the ointment by means of repeated applications, and after 48 hours from the beginning of the therapy the affected tissue had totally recovered its normal appearance.

$5^{th}$ case—Scald from boiling water—A woman showed a burn from water at the boiling point on her hand and forearm. In this case the ointment of the invention was applied on the affected zone after less than half an hour, and after 24 hours the cutaneous surface had reverted to a totally normal condition, and no blisters had formed on the concerned area. The present invention has been disclosed with particular reference to some specific embodiments thereof, but it should be understood that modifications and changes may be made by a person skilled in the art without departing from the scope of the invention as defined in the appended claims.

What is claimed is:

1. A composition for the topical treatment of burns, sunburns, abrasions, ulcers and cutaneous irritation, comprising, as active ingredients, chlorophyll, cod liver oil, camphor, and an antiseptic agent selected from the group consisting of niaouli oil, thyme oil, and mixtures thereof, the composition provided in a pharmaceutically acceptable vehicle for topical application, and wherein the composition comprises the following ingredients in the specified amounts (wherein the percentages are based on the total weight of the composition):

| | |
|---|---|
| chlorophyll | 0.5–5%, |
| cod liver oil | 5–10%, |
| camphor | 5–10%, |
| niaouli oil | 5–10%, and |
| thyme oil | 2–5%. |

2. The composition according to claim 1, having the following formulation:

| | |
|---|---|
| chlorophyll | 1%, |
| cod liver oil | 8%, |
| camphor | 8% |
| niaouli oil | 8%, |
| thyme oil | 2–5%, and |
| excipients | q.s. to 100%. |

3. The composition according to claim 2, wherein the excipients comprise one or more of the following ingredients: calendula oil, anhydrous lanolin, paraffin, white wax, sweet almond oil, boric acid and/or salts thereof, mono-, di-, and triglycerides of fatty acids, non-ionic surfactants, and polyethylene glycol.

4. The composition according to claim 3, wherein the excipient is anhydrous lanolin.

5. The composition according to claim 3, wherein the excipient is a mixture of boric acid, paraffin, white wax and sweet almond oil.

6. The composition according to claim 1, wherein the composition is in the form of an ointment, a salve, a cream, an emulsion or a gel.

7. A method of promoting skin healing, comprising topically administering to an area in need thereof an amount of the composition according to claim 1 effective to promote the desired skin healing.

8. A method of reactivating the epithelialization process, comprising topically administering to an area in need thereof an amount of the composition according to claim 1 effective to reactivate the epithelialization process.

9. A method of stimulating the reparative processes of skin tissue, comprising topically administering to an area in need thereof an amount of the composition according to claim 1 effective to stimulate the reparative processes of skin tissue.

10. A method of topically treating burns, sunburns, abrasions, ulcers and cutaneous irritation, comprising topically administering to an area in need of such treatment an effective amount of the composition according to claim 1.

11. A composition for the treatment of burns, sunburns, abrasions, ulcers and cutaneous irritation, consisting of (wherein the percentages are based on the total weight of the composition):

| | |
|---|---|
| chlorophyll | 1%, |
| cod liver oil | 8%, |
| camphor | 8% |
| niaouli oil | 8%, |
| thyme oil | 3.5%, and |
| anhydrous lanolin | q.s. to 100%. |

* * * * *